US008334398B2

(12) United States Patent
Gutsch et al.

(10) Patent No.: US 8,334,398 B2
(45) Date of Patent: Dec. 18, 2012

(54) COMPOUNDS AND METHODS FOR THE TREATMENT OF CANCER

(75) Inventors: Paul Gutsch, Gilbert, AZ (US); Brian Renzelmann, Waukesha, WI (US)

(73) Assignee: Ziopharm Oncology, Inc., Charlestown, MA (US)

( * ) Notice: Subject to any disclaimer, the term of this patent is extended or adjusted under 35 U.S.C. 154(b) by 0 days.

(21) Appl. No.: 13/150,516

(22) Filed: Jun. 1, 2011

(65) Prior Publication Data
US 2012/0022229 A1    Jan. 26, 2012

Related U.S. Application Data

(63) Continuation of application No. 11/495,172, filed on Jul. 28, 2006, now Pat. No. 7,968,738.

(60) Provisional application No. 60/704,163, filed on Jul. 29, 2005.

(51) Int. Cl.
*C07C 229/26* (2006.01)
(52) U.S. Cl. ........................................................ 556/70
(58) Field of Classification Search .................. None
See application file for complete search history.

(56) References Cited

U.S. PATENT DOCUMENTS

| 6,191,123 | B1 | 2/2001 | Uckun et al. |
| 6,482,815 | B1 | 11/2002 | Uckun et al. |
| 6,482,816 | B1 | 11/2002 | Uckun et al. |
| 6,911,471 | B2 | 6/2005 | Zingaro et al. |
| 6,995,188 | B2 | 2/2006 | Zingaro et al. |
| 7,619,000 | B2 | 11/2009 | Zingaro et al. |
| 2002/0013371 | A1 | 1/2002 | Warrell et al. |
| 2002/0183385 | A1 | 12/2002 | Ellison et al. |
| 2003/0176359 | A1 | 9/2003 | Neuwelt et al. |
| 2004/0028750 | A1 | 2/2004 | Lu |
| 2004/0034095 | A1* | 2/2004 | Zingaro et al. ............... 514/504 |
| 2005/0131062 | A1 | 6/2005 | Zingaro et al. |

FOREIGN PATENT DOCUMENTS

| EP | 1002537 A1 | 5/2000 |
| SU | 188 971 | 11/1966 |
| WO | WO-99/24029 A1 | 5/1999 |
| WO | WO-03/057012 A2 | 7/2003 |
| WO | WO-2006/020048 A2 | 2/2006 |

OTHER PUBLICATIONS

American Conference of Governmental Industrial Hygienists, Inc. (ACGIH). Arsenic and soluble compounds, including arsine. Documentation of the Threshold Limit Values and Biological Exposure Indices, sixth edition, 1991.
Aslanidis, et al., "Methylarsino-substituted hydroxy carboxylate esters," Chemiker-Zeitung, 112(4):125-127 (1988).
Bachleitner-Hofmann et al., "Arsenic trioxide and ascorbic acid: synergy with potential implications for the treatment of acute myeloid leukaemia," Br. J. Haematol., 112(3):783-786 (2001).
Banks, et al., "Biomolecules Bearing the S- or SeAsMe2 Function: Amino Acid and Steroid Derivatives," Jr. of Medicinal Chemistry, American Chemical Society, 22(5):572-575 (1979).
Barber, Harry J., "Hydrolysis of arylthioarsinites Hydrolysis of arylthioarsinites," Jr. of the Chemical Society, Abstracts 1365-9 (1932).
Beckermann, "Determination of monovethylarsonic acid and dimethylarsinic acid by derivatization with thioglycolic acid methyl ester and gas-liquid chromatographic separation," Analytica Chimica Acta, 135(1):77-84 (1982).
Beliles, "The Metals", In Patty's Industrial Hygiene and Toxicology, fourth edition G.D. Clayton and F.E. Clayton, eds. John Wiley & Sons, Inc.: New York. pp. 1913-1925 (1994).
Caira, M.R., "Crystalline Polymorphism of Organic Compounds," Topics in Current Chemistry, 198:163-208 (1998).
Calleja and Warrell, "Differentiating agents in pediatric malignancies: all-trans-retinoic acid and arsenic in acute promyelocytic leukemia," Curr. Oncol. Rep., 2:519-523 (2000).
Chen, et al., "6-thio-and-seleno-alpha-D-glucose esters of dimethylarsinous acid," Carb. Res. 50:53-62 (1976).
Chen, et al., "Synthesis of 1- and 6-S and 1- and 6-Se-derivatives of 2-amino-2-deoxy-alpha/beta-D-glucopyrasone," J. Chemical Soc, Perkin Trans., 1:2287-2293 (1980).
Cullen, et al.,"The metabolism of methylarsine oxide and sulfide," Applied Organometallic Chemistry, 3(1):71-78 (1989).
Cullen, et al., "The reaction of methylarsenicals with thiols: some biological implications," Journal of Inorganic Biochemistry, 21(3):179-194 (1984).
Cuzick, et al., "Medicinal arsenic and internal malignancies," Br. J. Cancer, 45:904-911 (1982).
Daniel, et al., "Dimethylarsinous Acid Esters of 1-Thio- and -Selenogalactose, A New Class of Potential Carcinostatic Agents," Phosphorus and Sulfur, 4:179-185 (1978).
Emran, et al., "Synthesis and biodistribution of radioarsenic labeled dimethylarsinothiols: derivatives of pennicillamine and mercaptoethanol," International Journal of Nuclear Medicine and Biology, 11(3-4):259-261 (1984).
Fatouros, et al., "Preparation and properties of arsonolipid containing liposomes," Chemistry and Physics of Lipids, 109:75-89 (2001).
Forkner and McNair-Scott, "Arsenic as a therapeutic agent in chronic myeloid leukemia," JAMA, 97(1):3-6 (1931).
Gao et al., "Synthesis of S-dialkylarsino-3-mercapto-1,2-propanediols and evaluation of their anticancer activity," Bioorg. Med. Chem., 15(7):2660-2666 (2007).
Geissler, et al., "In vivo effects of arsenic trioxide in refractory acute myeloid leukemia other than acute promyelocytic leukemia," Blood, 94:4230a (1999).
Gillard, et al., "Amylo-1,6-glucosidase/4-.alpha.-glucanotransferase," The Journal of Biological Chemistry, 255(18): 8451-8457 (1980).
Goyer, "Toxic effects of metals" In Casarett and Doull's Toxicology: The Basic Science of Poisons, 5th edition. C.D. Klassen, ed. McGraw-Hill: New York, pp. 691-698 (1996).

(Continued)

*Primary Examiner* — Yevegeny Valenrod
(74) *Attorney, Agent, or Firm* — Wilmer Cutler Pickering Hald and Dorr LLP

(57) ABSTRACT

The present invention provides organic arsenicals. Many of these compounds have potent in vitro cytotoxic activity against numerous human tumor cell lines, both of solid and hematological origin, as well as against malignant blood cells from patients with leukemia.

9 Claims, No Drawings

OTHER PUBLICATIONS

Grignani, et al., "The acute promyelocytic leukemia-specific PML-RAR alpha fusion protein inhibits differentiation and promotes survival of myeloid precursor cells," Cell, 74:423-431 (1993).

Hirano S. et al., "Cytotoxic effects of S-(dimethylarsino)-glutathione: a putative intermediate metabolite of inorganic arsenicals," Toxicology. Oct. 3, 2006 (Epub. Jul. 14, 2006), 227(1-2):45-52.

Hosain, et al., "Synthesis of radioarsenic labeled dimethylchloroarsine for derivation of a new group of radiopharmceuticals," International Journal of Applied Radiation and Isotopes, 33(12):1477-1478 (1982).

Hughes and Kenyon, "Dose-dependent effects on the disposition of monomethylarsonic acid and dimethylarsinic acid in the mouse after intravenous administration," J. Toxicol. Environ. Health, 53(2):95-112 (1998).

Iarc. Some metals and metallic compounds. IARC Monographs on the Evaluation of the Carcinogenic Risk of Chemicals to Man. vol. 23:39-141 (1980).

Ionov, et al., "Reaction of tertiary arsine sulfides with alkyl chlorocarbonates," Zhurnal Obshchei Khimii, 46(11):2555-2558 (1976).

Kala, et al., "The MRP2/cMOAT transporter and arsenic-glutathione complex formation are required for bilary excretion of arsenic," J. Biol. Chem., 275(43):33404-33408 (2000).

King and Ludford, "Relation between the constitution of arsenicals and their action on cell division," Journal of the Chemical Society Abstracts, 2086-2088 (1950).

Kitamura, et al., "New retinoids and arsenic compounds for the treatment of refractory acute promyelocytic leukemia: clinical and basic studies for the next generation," Cancer Chemother Pharmacol., 40 (Suppl):S36-S41 (1997).

Knock, et al., "The use of selected sulfhydryl inhibitors in a preferential drug attack on cancer," Surg. Gynecol. Obstet., 133:458-466 (1971).

Kober, et al., "Reaction of (dimethylamino)dimethylarsine with 1, 2-diols Reaction of (dimethylamino)dimethylarsine with 1, 2-diols," Zeitschrift Fuer Anorganische Und Allgemeine Chemie, 406(1):52-61 (1974).

Konig, A., et al., "Comparative activity of melarsoprol and arsenic trioxide in chronic B-cell leukemia lines," Blood 90:562-570 (1997).

Lallemand-Breitenbach, et al., "Retinoic acid and arsenic synergize to eradicate leukemic cells in a mouse model of acute promyelocytic leukemia," J. Exp. Med., 189:1043-1052 (1999).

Lam, et al., "Spectroscopic studies of arsenic (III) binding to *Escherichia coli* RI methyltransferase and to two mutants, C223S and W183F," Biochemistry, 31(43):10438-10442 (1992).

Lin, et al., "Methylarsenicals and arsinothiols are potent inhibitors of mouse liver thioredoxin reductase," Chemical Research in Toxicology, 12(10):924-930 (1999).

Mester, et al., "Speciation of dimethylarsinic acid and monomethylarsonic acid by gas chromatography-mass spectrometry," Jr. of Chromatography, 832(1+2):183-190 (1999).

Mountain, et al., "Chemotherapy studies in an animal tumor spectrum: II. Sensitivity of tumors to fourteen antitumor chemicals," Cancer Res., 26:181-206 (1966).

Raab et al., "Arsenic-glutathione complexes-their stability in solution and during separation by different HPLC modes," J. Anal. At. Spectrom., 19(1):183-190 (2004).

Rivi, et al., "Organic arsenical melarsoprol shows growth suppressive activity via programmed cell death on myeloid and lymphoid leukemia derived cell lines," Blood (Suppl), 88:68a (1996).

Rosenthal, et al., "The Synthesis and Characterization of Thio Sugar Esters of Diorganylarsinous Acids," Phosphorus and Sulfur, 9:107-116 (1980).

Rousselot, et al., "Use of arsenic trioxide (As$_2$O$_3$) in the treatment of chronic myelogenous leukemia: In vitro and in vivo studies," Blood, 94:4457a (1999).

Sakurai T. et al., "Toxicity of a trivalent organic arsenic compound, dimethylarsinous glutathione in a rat liver cell line (TRL 1215)," Br J Pharmacol. Dec. 2006 (Epub. Oct. 16, 2006), 149(7):888-897.

Schoene, et al, "Speciation of arsenic-containing chemical warfare agents by gas chromatographic analysis after derivatization with thioglcolic acid methyl ester," Journal of Chromatography, 605(2):257-262 (1992).

Scott, et al., "Reactions of arsenic (III) and arsenic (V) species with glutathione," Chemical Research in Toxicology, 6(1):102-106 (1993).

Soignet, et al., "Clinical study of an organic arsenic melarsoprol, in patients with advanced leukemia," Cancer Chemother. Pharmacol. 44:417-421 (1999).

Soignet, et al., "Dose-ranging and clinical pharmacologic study of arsenic trioxide in patients with advanced hematologic cancers," Blood, 94:1247a (1999).

Styblo, et al., "Comparative inhibition of yeast glutathione reductase by arsenicals and arsenothiols," Chemical Research in Toxicology, 10(1):27-33 (1997).

Tallman, "Therapy of acute promyelocytic leukemia: all-tans retinoic acid and beyond," Leukemia, 12 (Suppl 1):S37-S40 (1998).

Tsalev, et al., "Flow-injection hydride generation atomic absorption spectrometric study of the automated on-line pre-reduction of arsenate, methylarsonate and dimethylarsinate and high-performance liquid chromatographic separation of theirl-cysteine complexes," Talanta, 51(6):1059-1068 (2000).

Tsao, et al., "Optically Detected Magnetic Resonance Study of the Interaction of an Arsenic(III) Derivative of Cacodylic Acid with EcoRI Methyl Transferase," Biochemistry, 30(18):4565-72 (1991).

Vega, et al., "Differential effects of trivalent and pentavalent arsenicals on cell proliferation and cytokine secretion in normal human epiderman keratinocytes," Toxicology and Applied Pharmacology, 172(3):225-232 (2001).

West, Anthony R., solid state chemistry and applications, Wiley, New York, 1988, pp. 358 and 365.

Wiernik, et al., "Phase II trial of arsenic trioxide (As$_2$O$_3$) in patientis with relapsed/refractory acute myeloid leukemia, last crisis of CML or myelodysplasia," Blood, 94:2283a (1999).

Zhang, et al., "Arsenic trioxide treated 72 cases of acute promyelocytic leukemia," Chin. J. Hematol., 17:58-62 (1996).

Zingaro et al., "Thio and Seleno Sugar Esters of Dialkylarsinous Acids," Carbohydrate Research, 29:147-152 (1973).

Zingaro, Ralph A., "Seleno and Thio Sugar Esters of Group VA Acids," Chemica Scripta, 8A: 51-57 (1975).

Craig et al.: "Phase II trial of darinaparsin in leukemias and lymphomas," AACR Meeting Abstracts Online, Apr. 2008, XP000002657429, Retrieved from the Internet: URL:http://www.aacrmeetingabstracts.org/cgi/content/meeting_abstract/2008/1_Annual_Meeting/5527?maxtoshow=&hits=10&RESULTFOR-MAT=&author1=craig&andorexactfulltext=and&s earchid=1&FIRSTINDEX=0&sortspec=relevance&resourcetype=HWCIT [retrieved on Aug. 22, 2011] (2 pages).

* cited by examiner

COMPOUNDS AND METHODS FOR THE TREATMENT OF CANCER

CROSS REFERENCE TO RELATED APPLICATIONS

This application is a continuation of U.S. patent application Ser. No. 11/495,172, filed on Jul. 28, 2006, which claims the benefit of U.S. Provisional Application Ser. No. 60/704,163, filed Jul. 29, 2005. All of the teachings of the above-referenced applications are incorporated herein by reference.

FIELD OF THE INVENTION

The present invention relates generally to the field of anti-cancer therapy. More particularly, it provides organic arsenic compounds and methods for their use in treating cancers such as leukemia and solid tumors.

BACKGROUND OF THE INVENTION

Despite progress in leukemia therapy, most adult patients with leukemia still die from disease progression. Arsenic trioxide, an inorganic compound, has been approved for the treatment of patients with relapsed or refractory acute promyelocytic leukemia (APL) and is being evaluated as therapy for other leukemia types. Preliminary data from China and the recent experience in the U.S., however, suggest a role for arsenic trioxide in the other hematologic cancers as well. Consequently, the activity of arsenic trioxide as an anti-leukemic agent is currently being investigated in many types of leukemia. Although the results look favorable in terms of the response rate of some of the leukemia types that are being investigated, systemic toxicity of arsenic trioxide is a problem (Soignet et al., 1999; Wiernik et al., 1999; Geissler et al., 1999; Rousselot et al., 1999).

The only organic arsenical (OA) manufactured for human use, melarsoprol, has been evaluated for antileukemic activity (WO9924029, EP1002537). Unfortunately, this compound is excessively toxic to patients with leukemia at concentrations used for the treatment of trypanosomiasis. Therefore, there is a need to identify arsenic derivatives that can be used for the treatment of hematologic malignancies and cancer in general, that have similar or greater activity and lower toxicity than arsenic trioxide.

SUMMARY OF THE INVENTION

The present invention provides organic arsenical compounds with anti-cancer properties. In certain embodiments, the present invention provides compounds having a structure of formula (I) or a pharmaceutically acceptable salt thereof

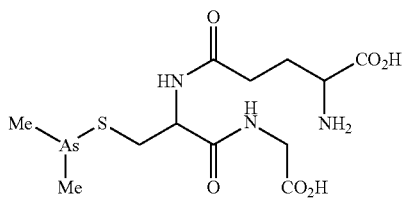

(I)

or a pharmaceutically acceptable salt thereof, wherein the melting point of the compound in its crystalline form is greater than 160° C.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a number of organic arsenic compounds.

In certain embodiments, the organic arsenicals of the present invention have a structure of formula (I) or a pharmaceutically acceptable salt thereof

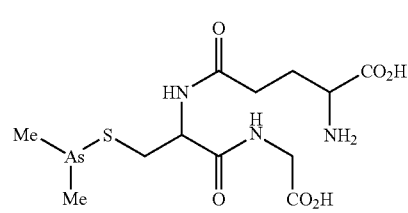

(I)

or a pharmaceutically acceptable salt thereof, wherein the melting point of the compound in its crystalline form is greater than 160° C., preferably greater than 170° C., more preferably greater than 180° C. In certain embodiments, the melting point of the compound in its crystalline form is in the range of about 160-220° C., preferably in the range of about 180-220° C., more preferably in the range of about 185-195° C. In certain embodiments, a compound of formula (I) is substantially free of pyridine hydrochloride.

If a chiral center is present, all isomeric forms are within the scope of the invention. Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5-6, pp 177-178, which section is hereby incorporated by reference.

Another aspect of the invention relates to a method for the synthesis of a compound of formula (II)

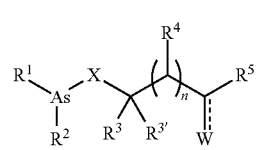

(II)

wherein
X is S or Se, preferably S;
W is O, S, or (R)(R), where each occurrence of R is independently H or a $C_{1-2}$alkyl, preferably O or (R)(R);
n is 0 or 1, preferably 1;
$R^1$ and $R^2$ are independently $C_{1-10}$alkyl, preferably $R^1$ and $R^2$ are independently selected from methyl, ethyl, propyl, and isopropyl;
$R^3$ is —H or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;

$R^4$ is —OH, —H, —CH$_3$, —OC(O)C$_{1-10}$aralkyl, —OC(O)C$_{1-10}$alkyl, —OC(O)aryl, or a glutamine;
$R^5$ is —OH, cyano, C$_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or C$_{1-10}$alkyl, preferably H,
wherein a compound having a structure of formula

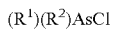

is reacted with a compound having a structure of formula (III)

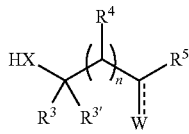

wherein
$R^3$ is —H or C$_{0-6}$alkyl-COOR$^6$;
$R^{3'}$ is H, amino, cyano, halogen, aryl, aralkyl, heteroaryl, heteroaralkyl, carboxyl, C$_{1-10}$alkyl, C$_{1-10}$alkenyl, or C$_{1-10}$alkynyl, preferably H;
$R^4$ is —OH, —H, —CH$_3$, —OC(O)C$_{1-10}$aralkyl, —OC(O)C$_{1-10}$alkyl, —OC(O)aryl, or a glutamine substituent;
$R^5$ is —OH, cyano, C$_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or C$_{1-10}$alkyl, preferably H;
in an aqueous or alcoholic solvent to provide a compound of formula (I).

In certain preferred embodiments, a compound of formula

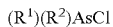

wherein $R^1$ and $R^2$ are independently C$_{1-10}$alkyl, preferably $R^1$ and $R^2$ are independently selected from methyl, ethyl, propyl, and isopropyl;
is reacted with a compound having a structure of formula

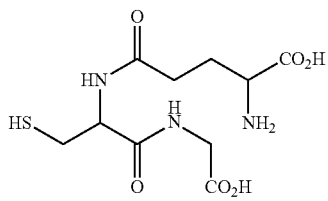

in an aqueous or alcoholic solvent system to provide a compound of formula (I). In certain preferred such embodiments, the solvent system comprises water and ethanol. In certain embodiments, the ratio of water to ethanol (v/v) is between about 4:1 and 1:4, preferably between about 2:1 and about 1:2. In certain preferred such embodiments, the ratio of water to ethanol (v/v) is about 1:1.

Another aspect of the invention relates to a method for purifying a compound of formula (II) admixed with pyridine hydrochloride, comprising
(a) combining the compound of formula (II) with enough ethanol to form a slurry,
(b) agitating the slurry for a period of time, and
(c) filtering the slurry.

In certain embodiments, a compound of formula (II) admixed with pyridine hydrochloride is slurried in ethanol, 200 pf., preferably under a nitrogen atmosphere.

In certain embodiments, the slurry is agitated for about 1 to about 24 hours. In certain preferred embodiments, the slurry is agitated for about 5 to about 15 hours, more preferably about 8 to about 12 hours.

In certain embodiments, the filtering further comprises washing. In certain embodiments, the washing is performed with ethanol. In certain preferred such embodiments, the washing is performed with ethanol and another polar organic solvent, preferably acetone.

In certain embodiments, the compound of formula (II) is

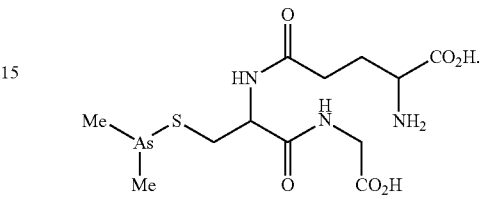

Another aspect of the invention relates to a method for the synthesis of a compound of formula

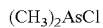

in a manner analogous to that shown in Example 1, wherein a compound having a structure of formula

is dissolved in a water/hydrochloric acid acid solution and hypophosphorus acid is slowly added to the solution.

The invention further provides pharmaceutical compositions comprising a compound of formula (I) or a pharmaceutically acceptable salt thereof, and a pharmaceutically acceptable diluent or carrier. In certain embodiments, the pharmaceutical composition is an aqueous solution that has a pH greater than about 4 or even greater than about 5, preferably in the range from about 4 to about 8 or even from about 5 to about 8, more preferably in the range from about 4 to about 7, or even about 5 to about 7.

In certain embodiments, the invention relates to pharmaceutical compositions comprising a compound of formula (I), or a pharmaceutically acceptable salt thereof, wherein the moisture content is less than about 10%, less than about 7%, less than about 5%, less than about 3%, ore even less than about 2%. In certain such embodiments, the pharmaceutical composition is a lyophilisate.

In certain such embodiments, the lyophilisate is prepared by lyophilization of an aqueous solution comprising a compound of formula (I) or a pharmaceutically acceptable salt thereof. In certain embodiments, the lyophilization is performed in less than about 72 hours, less than about 60 hours, less than about 48 hours, or even less than about 36 hours.

In certain embodiments, the lyophilization is performed by decreasing the temperature to about −30, about −35, about −40, about −45, or about −50° C. In certain such embodiments, the temperature is decreased at a rate of about 1.0, about 0.7, about 0.5, about 0.3, or about 0.1° C./min. In certain such embodiments, the composition is then held at a certain temperature as described herein for about 100, about 200, about 250, about 300, about 350, or about 400 minutes.

In certain embodiments, the composition is then subjected to a vacuum such that the pressure is about 200, about 100, about 75, about 50, or about 25 Ton. In certain such embodiments, the temperature is increased to about −10, about −5, about 0, about 5 or about 10° C. In certain such embodiments, the temperature is increased at a rate of about 0.5, about 0.3, about 0.1, or about 0.05° C./min. In certain such embodiments, the composition is held at a certain temperature and pressure as described herein for about 500, about 700, about 800, about 1000, about 1200, or about 1400 minutes.

In certain embodiments, the composition is then subjected to a vacuum such that the pressure is either raised or lowered in relation to the abovementioned vacuum pressure and the pressure is about 200, about 100, about 75, about 50, or about 25 Torr. In certain such embodiments the temperature is increased to about 15, about 20, about 25, about 30 or about 35° C. In certain such embodiments, the temperature is increased at a rate of about 0.5, about 0.3, about 0.1, or about 0.05° C./min. In certain such embodiments, the composition is held at a given temperature and pressure for about 600, about 700, about 720, about 740, about 760, about 780, about 800, or about 900 minutes.

Another aspect of the invention relates to a method for inhibiting cell proliferation, comprising contacting a cell with a compound of formula (I).

Another aspect of the invention provides a method for the treatment of cancer comprising administering a therapeutically effective amount of a compound of formula (I) as described above.

The invention also relates to the use of a compound of formula (I) as described above in the manufacture of a medicament for the treatment of cancer.

In certain embodiments, the cancer is selected from a solid tumor, such as brain, lung, liver, spleen, kidney, lymph node, small intestine, pancreas, blood cells, bone, colon, stomach, breast, endometrium, prostate, testicle, ovary, central nervous system, skin, head and neck, esophagus, or bone marrow, or a hematological cancer, such as leukemia, acute promyelocytic leukemia, lymphoma, multiple myeloma, myelodysplasia, myeloproliferative disease, or refractory anemia. In certain such embodiments, the cancer is a leukemia selected from acute and chronic leukemia.

Thus, in another aspect, the invention comprises a method of treating a patient with cancer comprising administering to the patient a composition comprising a compound of formula I or a pharmaceutical composition as described above. The therapeutically effective amount of a compound may be 0.1-1000 mg/kg, 1-500 mg/kg, or 10-100 mg/kg. In particular embodiments, the method may comprise administering the composition weekly, twice weekly, or even daily. It is further contemplated that treatment methods may involve multiple administrations daily. The method may comprise administering the compound daily such as by injection. Alternative routes and methods of administration described in the specification may also be used and the mode of administration will mainly depend on the type and location of the cancer. In certain embodiments, the method further comprises administering one or more additional agents to the patient. The additional agent may be all-trans-retinoic acid, 9-cis retinoic acid, Am-80, or ascorbic acid. The use of other adjunct cancer therapies, such as chemotherapy, radiotherapy, gene therapy, hormone therapy, and other cancer therapies known in the art are also contemplated in conjunction with the methods of the present invention.

Various methods of administration are contemplated, including regional, systemic, direct administration and by perfusion. Such methods include administration by injection, oral routes, intravenous, intraarterial, intratumoral, administration to tumoral vasculature, intraperitoneal, intratracheal, intramuscular, endoscopical, intralesional, percutaneous, subcutaneous, topical, nasal, buccal, mucosal, anogenital, rectal and the like.

DEFINITIONS

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substantially free", as used herein, refers to less than 5% by weight, preferably less than 2% by weight, more preferably less than 1% by weight.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

Cancer Treatment

The organic arsenicals of the current invention may be used to treat a variety of cancers, including all solid tumors and all hematological cancers, including leukemia, lymphoma, multiple myeloma, myelodysplasia, or myeloproliferative disorders. The OA can also be used to treat hematological cancers that have become refractory to other forms of treatment.

Leukemia is a malignant neoplasm of blood-forming tissues, characterized by abnormal proliferation of leukocytes and is one of the four major types of cancer. Leukemias are classified according to the type of leucocyte most prominently involved. Acute leukemias are predominantly undifferentiated cell populations and chronic leukemias have more mature cell forms (WO9924029).

The acute leukemias are divided into lymphoblastic (ALL) and non-lymphoblastic (ANLL) types and may be further subdivided by morphologic and cytochemical appearance according to the French-American-British classification or according to their type and degree of differentiation. Specific B- and T-cell, as well as myeloid cell surface markers/antigens are used in the classification too. ALL is predominantly a childhood disease while ANLL, also known as acute myeloid leukemia, is a more common acute leukemia among adults.

Chronic leukemias are divided into lymphocytic (CLL) and myeloid (CML) types. CLL is characterized by the increased number of mature lymphocytes in blood, bone marrow, and lymphoid organs. Most CLL patients have clonal expansion of lymphocytes with B cell characteristics. CLL is a disease of older persons. In CML, the granulocytic cells predominate at all stages of differentiation in blood and bone marrow, but may also affect liver, spleen, and other organs. Other malignant hematological disease that may be treated with the OA of the current invention, include, but are not limited to: myelodysplasia, myeloproliferative diseases, lymphomas, and multiple myeloma.

Pharmaceutical Compositions

The preparation of a pharmaceutical composition that contains at least one organic arsenical or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The organic arsenical may be combined with different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an organic arsenical compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The organic arsenical may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. Thus, preferred compositions have a pH greater than about 5, preferably from about 5 to about 8, more preferably from about 5 to about 7. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Combination Therapy

It is an aspect of this invention that the organic arsenical can be used in combination with another agent or therapy method, preferably another cancer treatment. The organic arsenical may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the organic arsenical. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the organic arsenical. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the organic arsenical is "A" and the secondary agent, which can be any other therapeutic agent, is "B":

A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery. The section below describes some adjunct cancer therapies:

Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristine, vinblastine and methotrexate, or any analog or derivative variant of the foregoing.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art will, in light of the present disclosure, appreciate that many changes can be made in the specific embodiments which are disclosed and still obtain a like or similar result without departing from the spirit and scope of the invention.

Example 1

Preparation of Dimethylchloroarsine

A 3 L, 3 necked round bottom flask was equipped with a mechanical stirrer assembly, an additional funnel, thermometer, nitrogen inlet, and a drying tube was placed in a bath. The flask was charged with cacodylic acid (250 g) and concentrated HCl (825 mL) and stirred to dissolve. After the cacodylic acid was completely dissolved, the solution was warmed to 40° C. To the stirring solution, hypophosphorous acid ($H_3PO_2$) (50% solution, 250 g) was added dropwise, maintaining the reaction temperature between 40-50° C. After approximately 50 mL of $H_3PO_2$ had been added, the solution became cloudy and the temperature of the reaction rose rapidly at which time an external cooling bath was used to maintain the reaction temperature between 40-50° C. The addition of the $H_3PO_2$ was continued, maintaining the reaction temperature in the desired range. After the addition of $H_3PO_2$ was complete, the reaction was held between 40-45° C. for 15 minutes while stirring. The external bath was removed and the stirring was continued. The reaction was allowed to stir and cool to <30° C. After the temperature of the reaction mixture dropped to 30° C. or less, methylene chloride (300 mL) was added and the resulting mixture was stirred to extract the product into the methylene chloride. Stirring was discontinued and the layers were allowed to separate over ½ hour. The layers were separated and the methylene chloride layer was dried over anhydrous sodium sulfate with stirring for a minimum of 1 hour. The mixture may be allowed to sit under a nitrogen atmosphere for a maximum of 72 hours. The organic mixture was filtered to remove the sodium sulfate and the methylene chloride was removed by atmospheric distillation. The crude residual product was distilled under a nitrogen atmosphere, through an 8" Vigreux or packed column. The product fraction with by 104-106° C. at atmospheric pressure was collected.

Example 2

Preparation of S-Dimethylarsinoglutathione

A 5 L, three necked round bottom flask was equipped with a mechanical stirrer assembly, thermometer, addition funnel, nitrogen inlet, and a drying tube was placed in a cooling bath. A polyethylene crock was charged with glutathione-reduced (200 g) and deionized water (2 L) and stirred under a nitrogen atmosphere to dissolve all solids. The mixture was filtered to remove any insoluble material and the filtrate was transferred to the 5 L flask. While stirring, ethanol, 200 proof (2 L) was added and the clear solution was cooled to 0-5° C. using an ice/methanol bath. Pyridine (120 g) was added followed by a dropwise addition of $Me_2AsCl$ (120 g) over a minimum of 1 hour. The reaction mixture was stirred at 0-5° C. for a minimum of 2 hours prior to removal of the cooling bath and allowing the mixture to warm to room temperature under a nitrogen atmosphere with stirring. The reaction mixture was stirred overnight (>15 hrs) at room temperature under a nitrogen atmosphere at which time a white solid may precipitate. The reaction mixture was concentrated to a slurry (liquid and solid) at 35-45° C. using oil pump vacuum to provide a white solid residue. As much water as possible is removed, followed by two coevaporations with ethanol to azeotrope the last traces of water. The white solid residue was slurried in ethanol, 200 pf. (5 L) under a nitrogen atmosphere at room temperature overnight. The white solid was filtered and washed with ethanol, 200 pf. (2×500 mL) followed by acetone, ACS (2×500 mL). The resulting solid was transferred to drying trays and vacuum oven dried overnight at 25-35° C. using oil pump vacuum to provide pyridinium hydrochloride-free S-dimethylarsinoglutathione as a white solid with a melting point of 189-190° C.

Example 3

Preparation of Dosage Form of S-Dimethylarsinoglutathione

A solution of S-dimethylarsinoglutathione in water for injection (WFI) was adjusted to pH 5.0 to 5.5 with NaOH or HCl. The resulting solution was then filtered through a 0.2 micron Sartopore 2 filter and a Flexicon filling unit was used to deliver 150 mg per Type 1 borosilicate glass vial (Wheaton). The filled vials were then lyophilized in a Hull 48

Lyophilizer unit by first loading the vials on the shelf and ramping the temperature to −40° C. at a cooling rate of 0.5° C. per minute. The shelf temperature was then held at −40° C. for 300 minutes. A vacuum was then applied at 75 micron and the shelf temperature was ramped up to 5° C. at a rate of 0.1° C. per minute. The shelf temperature was then held at 5° C. for 1,000 minutes before applying the vacuum at 50 micron. The shelf temperature was then ramped up to 25° C. at a rate of 0.1° C. per minute and the temperature was held at 25° C. for 720 minutes. The shelf temperature was then reduced to 5° C. and held until the final stoppering step, at which time the chamber was returned to 640,000 mm Torr with nitrogen and the vials were stoppered with gray butyl lyophilization stoppers and finally crimped with aluminum seals to provide S-dimethylarsinoglutathione as a white to off-white cake with a moisture content of 1.8%. The total time for the lyophilization procedure was 47 hours. The lyophilized S-dimethylarsinoglutathione was then reconstituted with 2.0 mL sterile water to provide a clear, colorless solution with a final concentration of 75±7.5 mg S-dimethylarsinoglutathione per mL and a pH of 4.5 to 6.0.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

We claim:
1. A process for the synthesis of a crystalline form of a compound having a structure of formula (II) or a pharmaceutically acceptable salt thereof

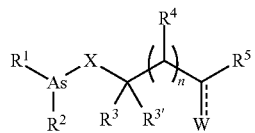
(II)

wherein
X is S or Se;
W is O, S, or (R)(R), where each occurrence of R is independently H or a $C_{1-2}$alkyl;
n is 0 or 1;
$R^1$ and $R^2$ are independently $C_{1-10}$alkyl;
$R^3$ is —H or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl;
$R^4$ is —OH, —H, —CH$_3$, —OC(O)C$_{1-10}$aralkyl, —OC(O)C$_{1-10}$alkyl, —OC(O)aryl, or a glutamine;
$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl;
wherein the melting point of the crystalline form is greater than 160° C.; comprising reacting a compound having a structure of formula

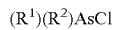
$(R^1)(R^2)AsCl$ wherein $R^1$ and $R^2$ are each methyl;

with a compound having the structure:

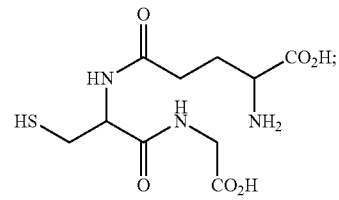

in an aqueous or alcoholic solvent system.
2. A method for the synthesis of a compound of formula (II)

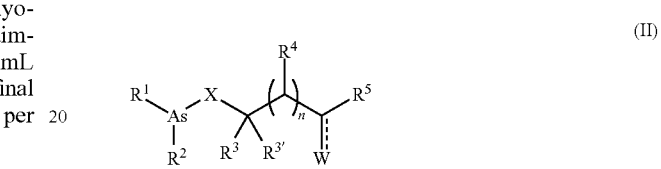
(II)

wherein
X is S or Se;
W is O, S, or (R)(R), where each occurrence of R is independently H or a $C_{1-2}$alkyl;
n is 0 or 1;
$R^1$ and $R^2$ are independently $C_{1-10}$alkyl;
$R^3$ is —H or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl;
$R^4$ is —OH, —H, —CH$_3$, —OC(O)C$_{1-10}$aralkyl, —OC(O)C$_{1-10}$alkyl, —OC(O)aryl, or a glutamine;
$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl;
wherein a compound having a structure of formula

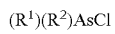
$(R^1)(R^2)AsCl$ $R^1$ and $R^2$ are independently $C_{1-10}$alkyl;
is reacted with a compound having a structure of formula (III)

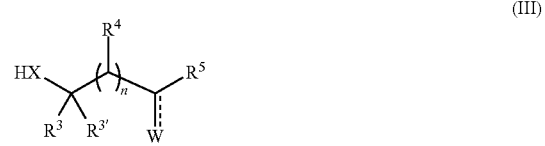
(III)

wherein
$R^3$ is —H or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl;
$R^4$ is —OH, —H, —CH$_3$, —OC(O)C$_{1-10}$aralkyl, —OC(O)C$_{1-10}$alkyl, —OC(O)aryl, or a glutamine substituent;
$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl;
in an aqueous or alcoholic solvent system.

3. A method of claim 2, wherein the compound of formula (III) has a structure

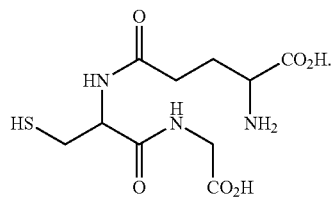

4. A method of claim 1, wherein the solvent system comprises ethanol and water.

5. A method of claim 1, wherein the compounds are reacted in the presence of pyridine and wherein the solvent system comprises ethanol and water.

6. A method of claim 2, wherein the solvent system comprises ethanol and water.

7. A method of claim 3, wherein the solvent system comprises ethanol and water.

8. A method of claim 2, wherein the compounds are reacted in the presence of pyridine and wherein the solvent system comprises ethanol and water.

9. A method of claim 3, wherein the compounds are reacted in the presence of pyridine and wherein the solvent system comprises ethanol and water.

* * * * *